(12) United States Patent
Okazaki et al.

(10) Patent No.: US 10,067,338 B2
(45) Date of Patent: Sep. 4, 2018

(54) OPTICAL FIBER SCANNER, ILLUMINATION DEVICE, AND OBSERVATION APPARATUS HAVING A HOLDING SECTION THAT CONDUCTS ELECTRICITY BETWEEN AN ELECTRICALLY CONDUCTIVE FRAME AND A PIEZOELECTRIC ELEMENT

(71) Applicant: OLYMPUS CORPORATION, Tokyo (JP)

(72) Inventors: Yoshiro Okazaki, Tokyo (JP); Yasuaki Kasai, Saitama (JP); Hiroshi Tsuruta, Kanagawa (JP); Hirokazu Yokota, Tokyo (JP); Kazutoshi Kumagai, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 176 days.

(21) Appl. No.: 15/299,534

(22) Filed: Oct. 21, 2016

(65) Prior Publication Data
US 2017/0038580 A1    Feb. 9, 2017

Related U.S. Application Data

(63) Continuation of application No. PCT/JP2015/057228, filed on Mar. 12, 2015.

(30) Foreign Application Priority Data

May 29, 2014    (JP) ................................ 2014-111376

(51) Int. Cl.
*A61B 1/00*    (2006.01)
*G02B 26/10*    (2006.01)
(Continued)

(52) U.S. Cl.
CPC .......... *G02B 26/103* (2013.01); *A61B 1/0017* (2013.01); *A61B 1/00172* (2013.01);
(Continued)

(58) Field of Classification Search
CPC ...... A61B 1/00172; A61B 1/07; G02B 26/103
(Continued)

(56) References Cited

U.S. PATENT DOCUMENTS 7,129,472 B1 * 10/2006 Okawa ............... A61B 1/00059
250/234
2014/0114131 A1    4/2014 Sakai et al.
2015/0029570 A1    1/2015 Ito et al.

FOREIGN PATENT DOCUMENTS

JP    2013-180078 A    9/2013
JP    2013-192825 A    9/2013
(Continued)

OTHER PUBLICATIONS

International Search Report dated Jun. 2, 2015 issued in PCT/JP2015/057228.

*Primary Examiner* — Que T Le
(74) *Attorney, Agent, or Firm* — Scully, Scott, Murphy & Presser, P.C.

(57) ABSTRACT

An optical fiber scanner including: an optical fiber that guides illumination light; a piezoelectric element that is disposed at an intermediate position on the optical fiber in the long-axis direction and that displaces, due to a bending vibration, an emission end of the optical fiber in a direction intersecting the long axis; a wiring part that is electrically bonded to the piezoelectric element at a location between the piezoelectric element and the optical fiber; a tube-shaped electrically conductive frame that has an inner hole for accommodating the piezoelectric element and the optical fiber; and a holding section that fixes the frame and the
(Continued)

piezoelectric element and that conducts electricity between the frame and the piezoelectric element.

9 Claims, 11 Drawing Sheets

(51) Int. Cl.
 *A61B 1/07* (2006.01)
 *G02B 23/24* (2006.01)
(52) U.S. Cl.
 CPC ............ *A61B 1/07* (2013.01); *G02B 23/2469* (2013.01); *G02B 23/2476* (2013.01)
(58) Field of Classification Search
 USPC .................................................. 250/235, 239
 See application file for complete search history.

(56) References Cited

FOREIGN PATENT DOCUMENTS

JP          2013-244045  A    12/2013
JP             5452781  B1     3/2014

* cited by examiner

OPTICAL FIBER SCANNER, ILLUMINATION DEVICE, AND OBSERVATION APPARATUS HAVING A HOLDING SECTION THAT CONDUCTS ELECTRICITY BETWEEN AN ELECTRICALLY CONDUCTIVE FRAME AND A PIEZOELECTRIC ELEMENT

CROSS-REFERENCE TO RELATED APPLICATIONS

This is a continuation of International Application PCT/JP2015/057228 which is hereby incorporated by reference herein in its entirety.

This application is based on Japanese Patent Application No. 2014-111376, the contents of which are incorporated herein by reference.

TECHNICAL FIELD

The present invention relates to an optical fiber scanner, an illumination device, and an observation apparatus.

BACKGROUND ART

There is a conventionally-known optical fiber scanner for scanning illumination light by displacing an emission end of an optical fiber, which guides light from a light source, due to bending vibrations of piezoelectric elements (for example, see PTL 1).

This optical fiber scanner is configured such that plate-like piezoelectric elements are fixed to four outer faces of a square-tube-shaped electrically conductive ferrule through which an optical fiber passes, the ferrule is set to have a common ground potential, and an electrical current is applied to the ferrule from lead wires fixed to the surfaces of the piezoelectric elements, which are located at the outer sides in the radial direction when viewed from the optical fiber, via the piezoelectric elements, thereby driving the piezoelectric elements.

CITATION LIST

Patent Literature

{PTL 1} Publication of Japanese Patent No. 5452781

SUMMARY OF INVENTION

Solution to Problem

According to one aspect, the present invention provides an optical fiber scanner including: an optical fiber that guides illumination light; a piezoelectric element that is disposed at an intermediate position on the optical fiber in the long-axis direction and that displaces, due to a bending vibration, an emission end of the optical fiber in a direction intersecting the long axis; a wiring part that is electrically bonded to the piezoelectric element at a location between the piezoelectric element and the optical fiber; a tube-shaped electrically conductive frame that has an inner hole for accommodating the piezoelectric element and the optical fiber; and a holding section that fixes the frame and the piezoelectric element and that conducts electricity between the frame and the piezoelectric element.

DESCRIPTION OF EMBODIMENTS

An optical fiber scanner 1 according to one embodiment of the present invention will be described below with reference to the drawings.

Figure 1:
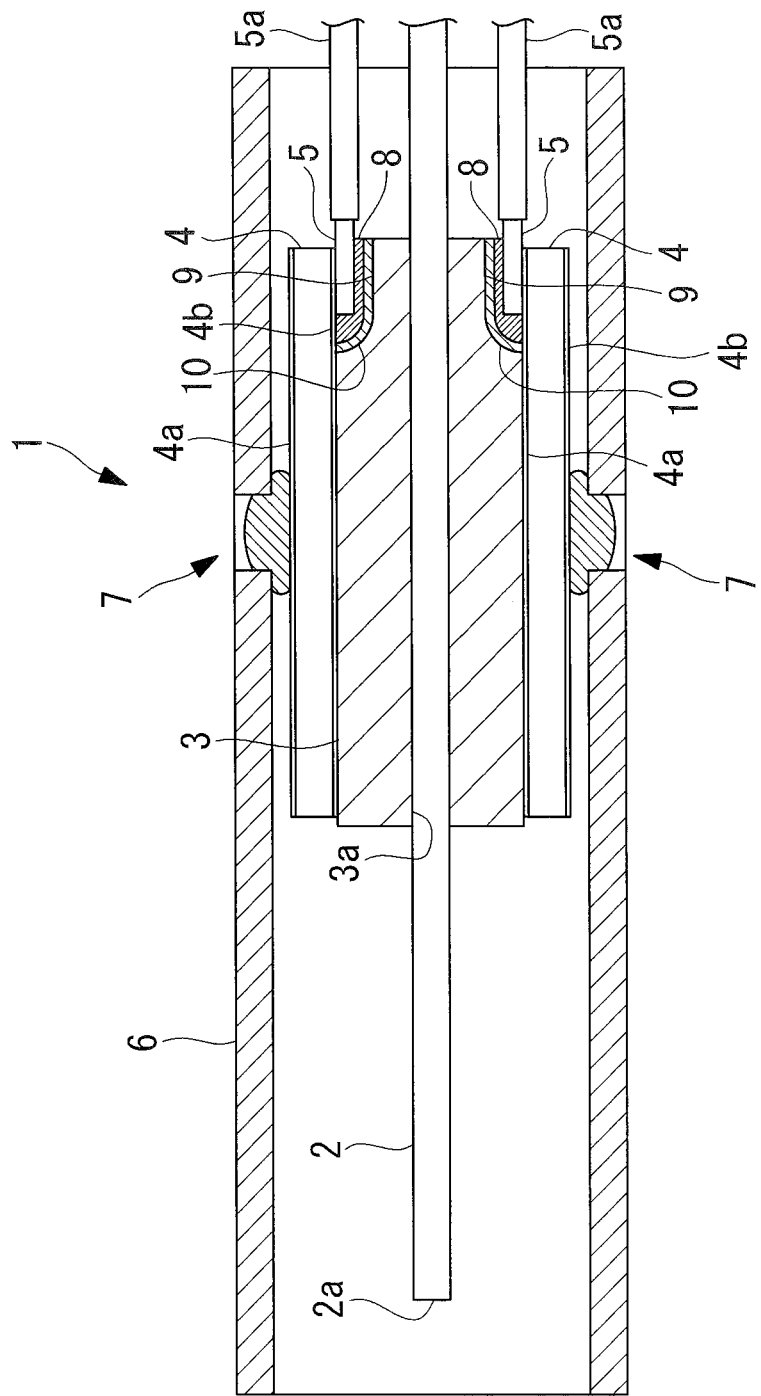
FIG. 1 is a longitudinal sectional view showing an optical fiber scanner according to one embodiment of the present invention.

As shown in FIG. 1, the optical fiber scanner 1 of this embodiment is provided with: an optical fiber 2 that guides illumination light; a square-tube-shaped ferrule (vibration transmission member) 3 that has a through-hole 3a through which the optical fiber 2 passes; four piezoelectric elements 4 that are fixed to four outer faces of the ferrule 3; lead wires 5 that supply electric power to the respective piezoelectric elements 4; a tube-shaped frame 6 that accommodates the assembly of the piezoelectric elements 4, the ferrule 3, and the optical fiber 2; and holding sections 7 that fix the frame 6 and the assembly.

A light source (not shown) is connected to one end of the optical fiber 2, and an emission end 2a from which illumination light from the light source is emitted is formed at the other end thereof.

The piezoelectric elements 4 are each formed by sandwiching a piezoelectric material between two parallel electrodes 4a and 4b, and the direction of polarization is set in one direction along the thickness direction thereof.

The ferrule 3 is formed of an elastic material having electrical insulation properties. The four piezoelectric elements 4 are fixed, by an adhesive, with the directions of polarization being aligned, such that the two piezoelectric elements 4 located on the opposing outer faces of the ferrule 3 form a pair and produce the same bending vibration. Accordingly, the two pairs of the piezoelectric elements 4 can produce bending vibrations in mutually orthogonal directions.

Figure 3:
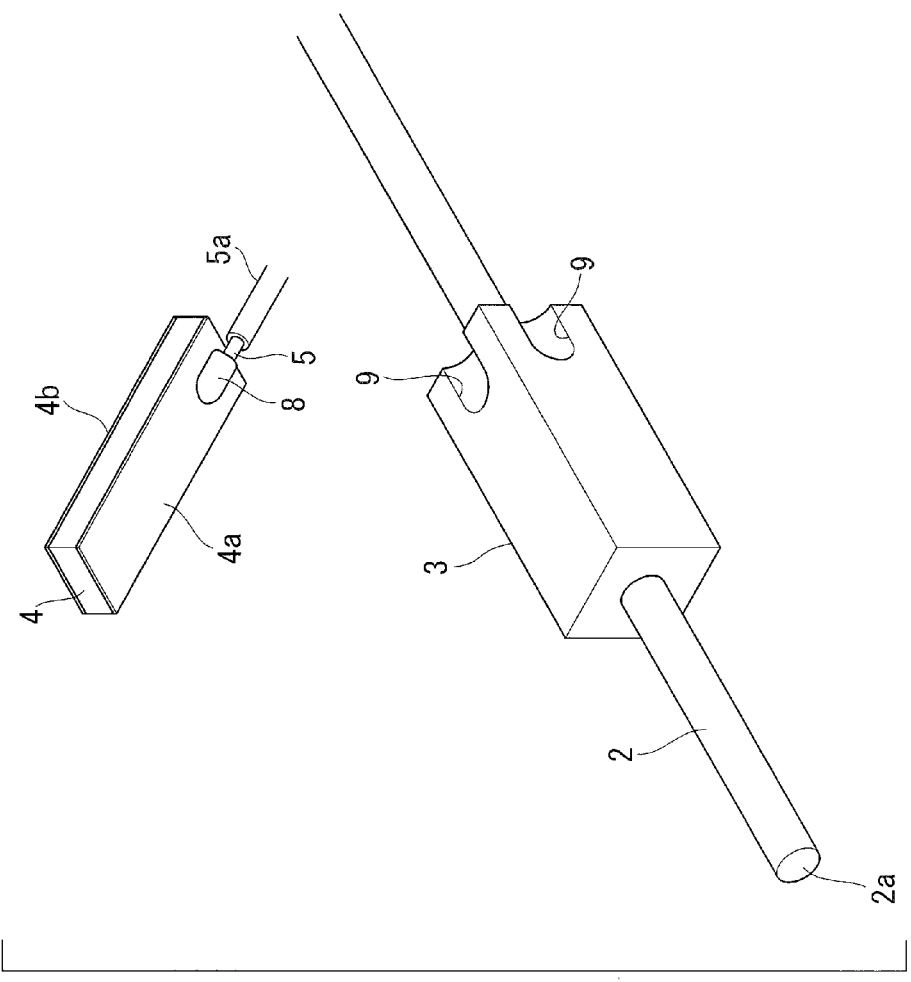
FIG. 3 is a perspective view for explaining the relationship between a ferrule and a piezoelectric element constituting the optical fiber scanner shown in FIG. 1.

As shown in FIG. 3, the lead wire 5 is bonded, by an electrically conductive adhesive or solder, to the electrode 4a or 4b, which is to be bonded to the ferrule 3, of the piezoelectric element 4. In the figure, reference sign 5a denotes an insulating coating for the lead wire 5. Furthermore, reference sign 8 denotes a joint part formed of an electrically conductive adhesive mass or solder fillet.

Figure 2:
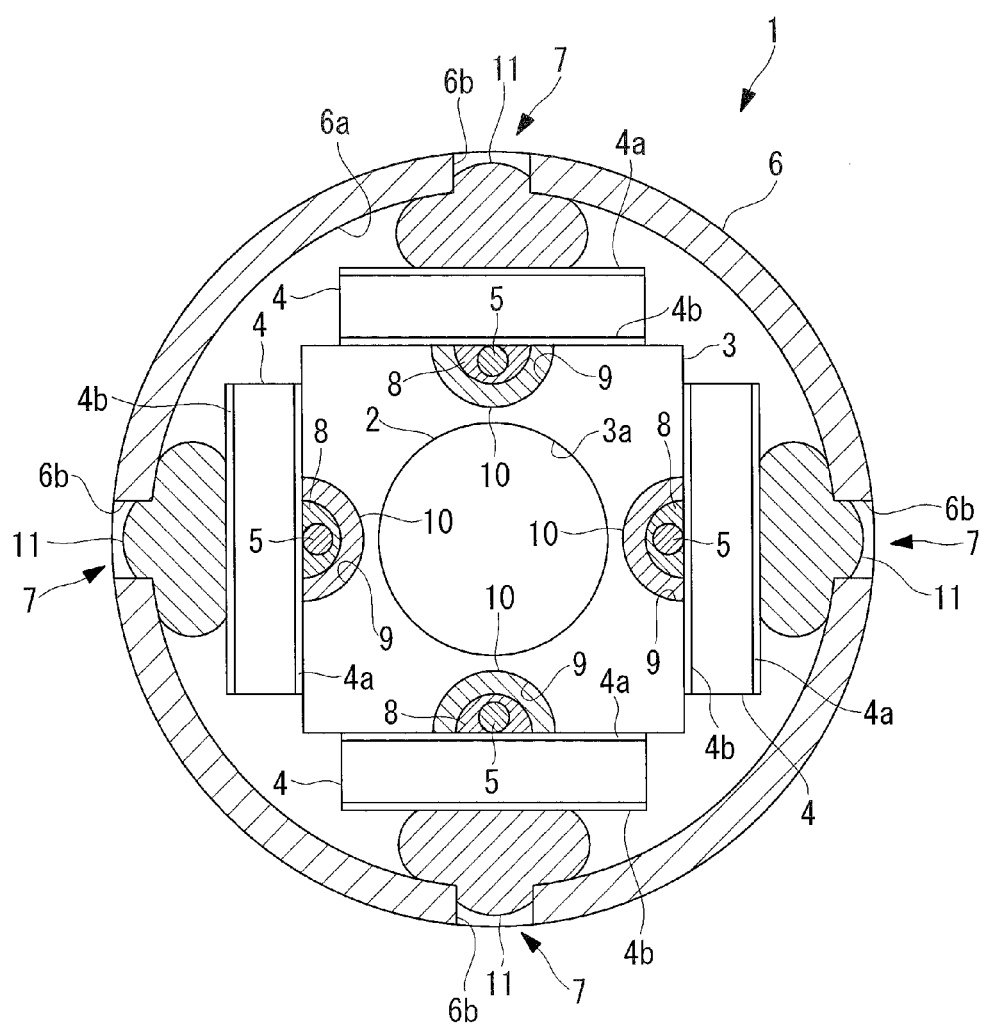
FIG. 2 is a transverse sectional view of the optical fiber scanner shown in FIG. 1, viewed from a base end.

In the four outer faces of the ferrule 3, concave sections 9 that can accommodate the joint parts 8 are formed at positions that correspond to the joint parts 8 of the lead wires 5 when the piezoelectric elements 4 are attached to the ferrule 3. As shown in FIGS. 1 and 2, part of an adhesive 10 that bonds the piezoelectric elements 4 to the ferrule 3 is filled in the concave sections 9, to fill up gaps between the concave sections 9 and the joint parts 8.

The tube-shaped frame 6 is formed of an electrically conducting material and is set to have a ground potential. Furthermore, the frame 6 is provided with through-holes 6b that radially penetrate the frame 6 from an inner hole 6a to the outer surface thereof, at four points that are located at an intermediate position in the longitudinal direction and at regular intervals in the circumferential direction.

The holding sections 7 are formed by hardening an electrically conductive adhesive 11 injected from the through-holes 6b of the frame 6 into the inner hole 6a of the frame 6, with the assembly of the ferrule 3 and the piezoelectric elements 4 being accommodated in the inner hole 6a of the frame 6. Accordingly, the holding sections 7 fix the assembly to the frame 6 and conduct electricity between the radially-outer electrodes 4a (4b) of the piezoelectric elements 4 and the frame 6.

Furthermore, in the example shown in FIG. 1, the holding sections 7 bond the piezoelectric elements 4 to the frame 6 at almost the center of the piezoelectric elements 4 in the longitudinal direction, and this position corresponds to nodes of the bending vibrations of the piezoelectric elements 4.

The operation of the thus-configured optical fiber scanner 1 of this embodiment will be described.

In order to activate the optical fiber scanner 1 of this embodiment, illumination light from the light source (not shown) is made to enter the optical fiber 2, and the illumination light guided in the optical fiber 2 is emitted from the emission end 2a.

Then, oscillatory voltages are applied between the electrodes 4a and 4b of the piezoelectric elements 4 via the lead wires 5, thereby causing the piezoelectric elements 4 to perform bending vibrations according to the periods and the amplitudes of oscillations of the voltages.

The piezoelectric elements 4 are fixed to the frame 6 by the holding sections 7 at the nodes of the bending vibrations, thus making it possible to perform bending vibrations without being disturbed.

The bending vibrations of the piezoelectric elements 4 are transferred to the optical fiber 2, which is supported in the through-hole 3a, via the ferrule 3, which is formed of an elastic member. Then, the optical fiber 2 is made to perform bending vibration, thereby allowing the emission end 2a to be displaced in directions intersecting the long axis.

Because the two pairs of piezoelectric elements 4 are provided such that bending vibrations are produced in mutually orthogonal directions, voltages with different oscillatory patterns are applied to the different pairs of piezoelectric elements 4, and the phases and the amplitudes of oscillations are adjusted, thereby making it possible to displace the emission end 2a of the optical fiber 2 according to a desired trajectory and to scan illumination light emitted from the emission end 2a along the trajectory according to the movement trajectory of the emission end 2a.

In this case, according to the optical fiber scanner 1 of this embodiment, because the lead wires 5 are connected to the electrodes 4a (4b) that are closer to the ferrule 3, and the frame 6 is set to have the ground potential, it is not necessary to worry about short circuits between the joint parts 8 of the lead wires 5 and the frame 6. Because the joint parts 8, which joint the lead wires 5 to the piezoelectric elements 4, are accommodated in the concave sections 9 provided in the ferrule 3, it is not necessary to provide sections that physically project farther radially outward than the piezoelectric elements 4 do.

Therefore, the inner-diameter size of the inner hole 6a of the frame 6 can be reduced to such an extent that the bending vibrations of the piezoelectric elements 4 are not disturbed. The displacement due to the bending vibrations of the piezoelectric elements 4 is on the order of micrometers, and thus, the inner diameter and outer diameter sizes of the frame 6 can be reduced to the utmost limit to achieve a reduction in diameter.

Furthermore, according to this embodiment, the holding sections 7 are located at an intermediate position in the longitudinal direction of the piezoelectric elements 4; therefore, it is also possible to reduce the size of the optical fiber scanner 1 in the long-axis direction, compared with a conventional case in which the piezoelectric elements 4 and the ferrule 3 are supported at an end portion in the longitudinal direction thereof. Accordingly, when the optical fiber scanner is used at a distal end of an insertion section of an endoscope, the size of a hard section to be located closer to the distal end than a joint is reduced, thereby making it possible to ensure a wide movement range in a narrow body cavity.

Figure 4:
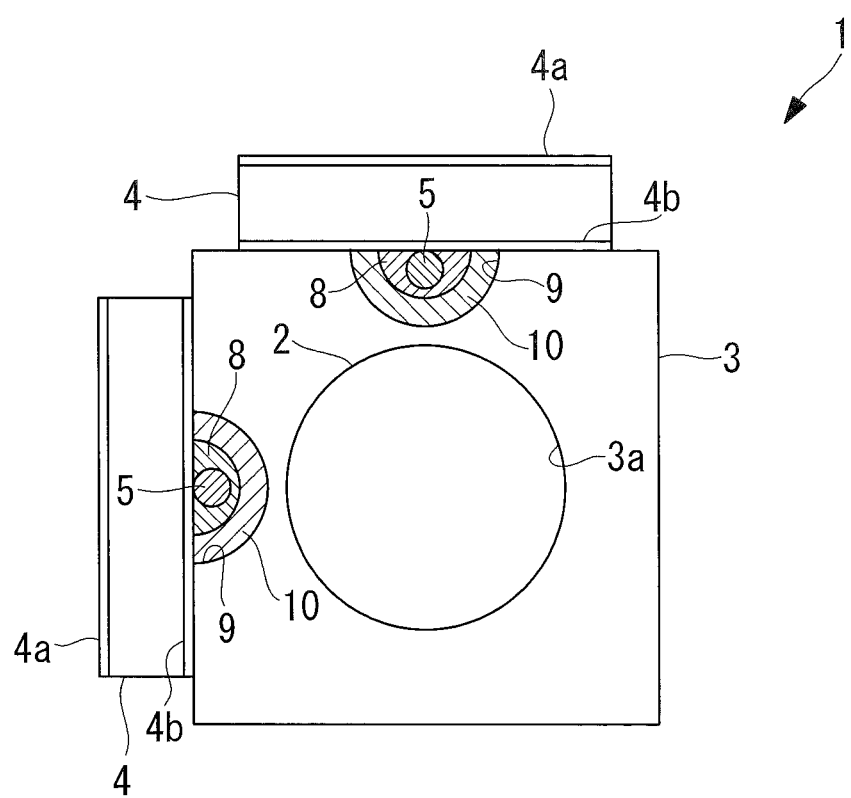
FIG. 4 is a transverse sectional view partially showing a first modification of the optical fiber scanner shown in FIG. 1.

Note that, in this embodiment, the piezoelectric elements 4 are disposed on the four faces of the ferrule 3, and the two pairs of the four piezoelectric elements 4 produce bending vibrations in mutually orthogonal directions; however, instead of this, as shown in FIG. 4, only two piezoelectric elements 4 may be fixed to two faces of the ferrule 3 that are orthogonal to each other.

Figure 5:
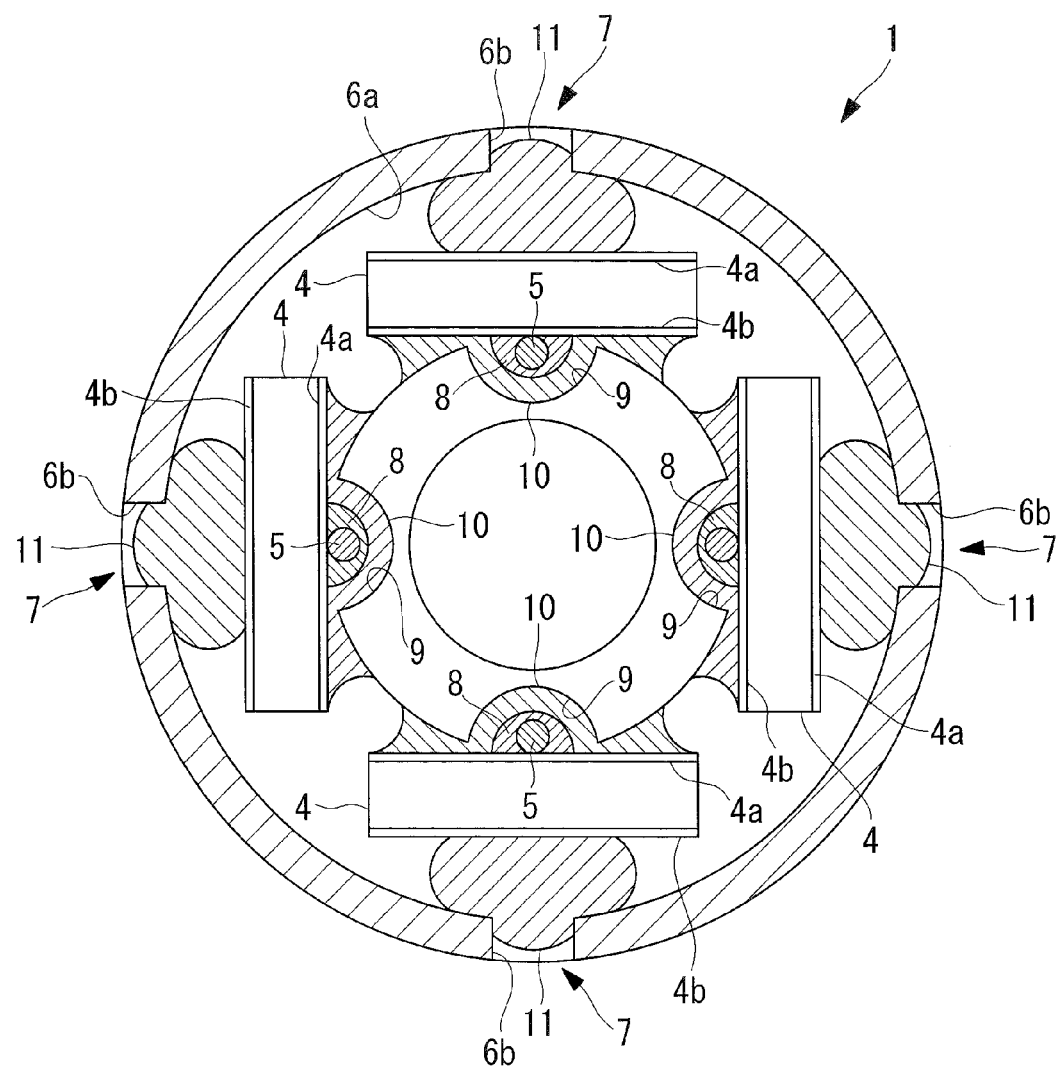
FIG. 5 is a transverse sectional view showing a second modification of the optical fiber scanner shown in FIG. 1.

Furthermore, instead of the square-tube-shaped ferrule 3, it is also possible to adopt a circular-tube-shaped ferrule, as shown in FIG. 5. In this case, the ferrule 3 and the piezoelectric elements 4 can be stably fixed by the adhesive 10. The circular-tube-shaped ferrule 3 can be subjected to more highly accurate processing.

Note that, in this case, it is also possible to adopt two piezoelectric elements 4 that produce bending vibrations in mutually orthogonal directions, instead of two pairs of the four piezoelectric elements 4.

Figure 6:
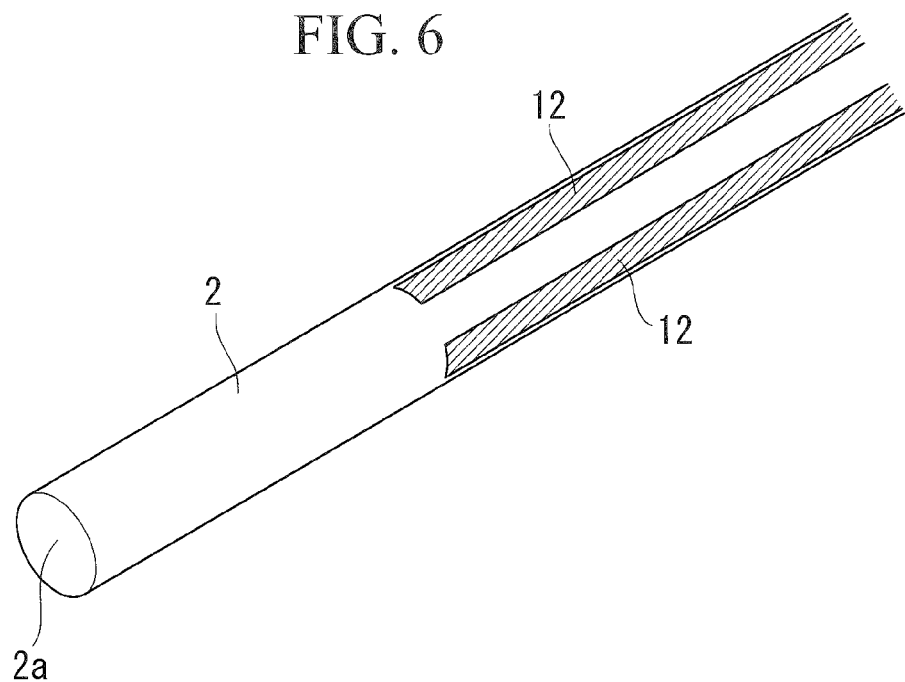
FIG. 6 is a perspective view of an optical fiber according to a third modification of the optical fiber scanner shown in FIG. 1.
Figure 7:
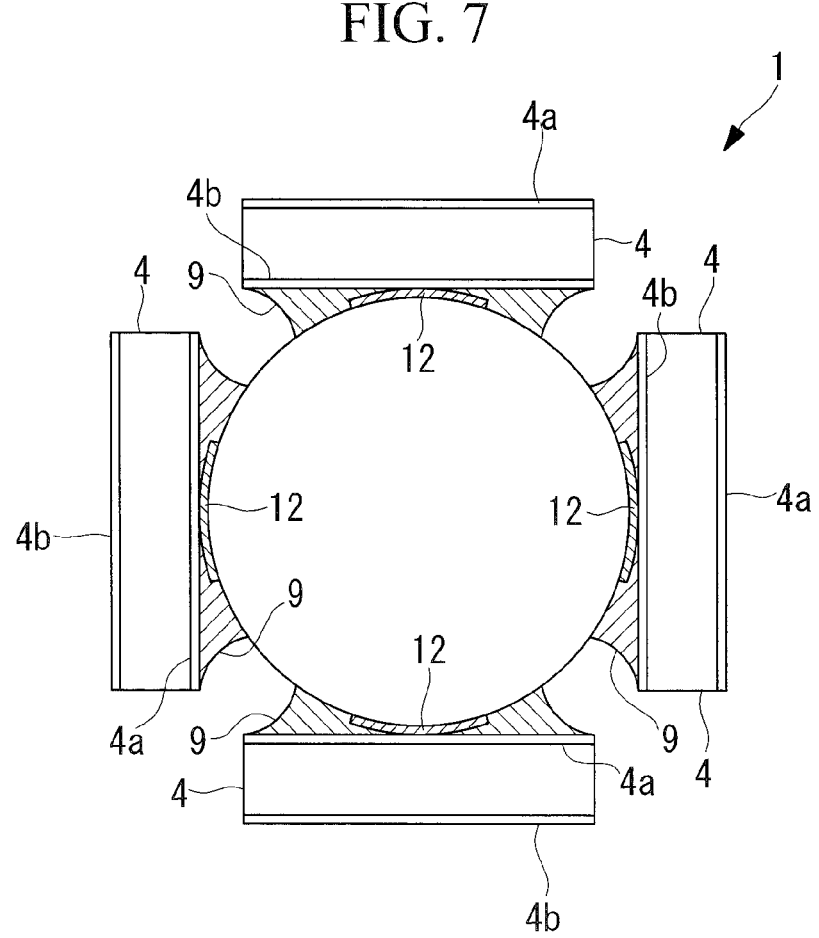
FIG. 7 is a transverse sectional view showing an optical fiber scanner using the optical fiber shown in FIG. 6.

Furthermore, in this embodiment, the ferrule 3 is disposed between the optical fiber 2 and the piezoelectric elements 4; however, instead of this, as shown in FIGS. 6 and 7, the piezoelectric elements 4 may be directly bonded to the outer periphery of the optical fiber 2. In this case, instead of the lead wires 5 serving as wiring parts, as shown in FIG. 6, a plurality of thin films 12 that are formed of an electrically conducting material can be formed on the outer surface of the optical fiber 2 at intervals in the circumferential direction, with elongated patterns extending in the long-axis direction, and the piezoelectric elements 4 can be bonded at the positions corresponding to the thin films 12 by joint parts 8 that are formed of an electrically conductive adhesive.

By doing so, there is an advantage that the space required for the ferrule 3 can be eliminated, thus achieving a further reduction in diameter.

The thin films 12 can be formed, for example, through thin-film formation performed by plating deposition processing or a sputtering method, or through application of an electrically conductive adhesive. The thin films 12 may be coated on the outer surface of the clad layer of the optical fiber 2 or may be formed on the surface of a resin coating that is usually used as a protective layer for the optical fiber 2.

Figure 8:
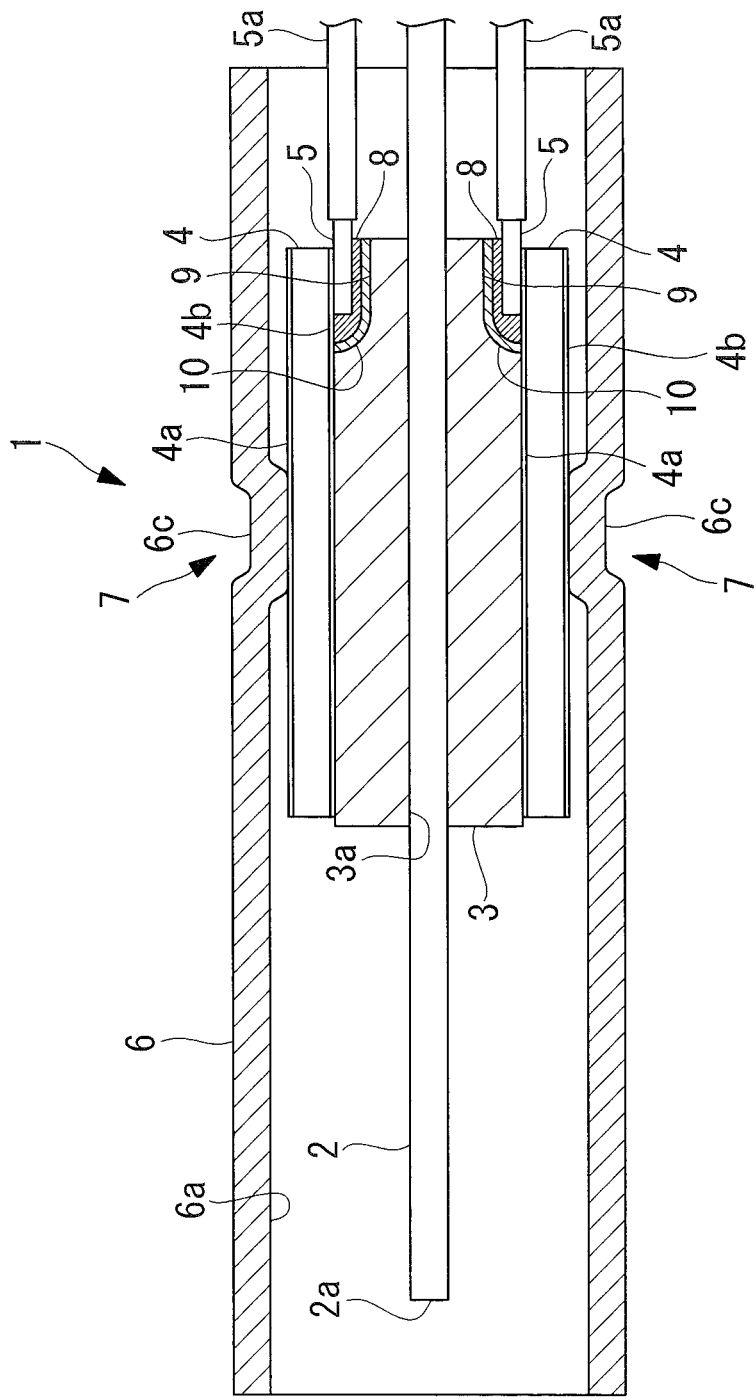
FIG. 8 is a longitudinal sectional view showing a fourth modification of the optical fiber scanner shown in FIG. 1.

Furthermore, in this embodiment, as the holding sections 7, the electrically conductive adhesives 11 are used to conduct electricity and mechanically fix between the electrodes 4a (4b) of the piezoelectric elements 4 and the frame 6; however, instead of this, as shown in FIG. 8, it is possible to form caulking sections 6c by pressing some parts of the frame 6 radially inward from outside, so that sections of the inner surface of the inner hole 6a corresponding to the caulking sections 6c are brought into close contact with the electrodes 4a (4b) of the piezoelectric elements 4, to realize both electrical conduction and mechanical fixing therebetween at the same time. Note that, since the piezoelectric elements 4 are fragile, conductive films (not shown) may be applied to the surfaces of the electrodes 4a and 4b, to distribute the stress imposed on the piezoelectric elements 4 during caulking.

Figure 9:
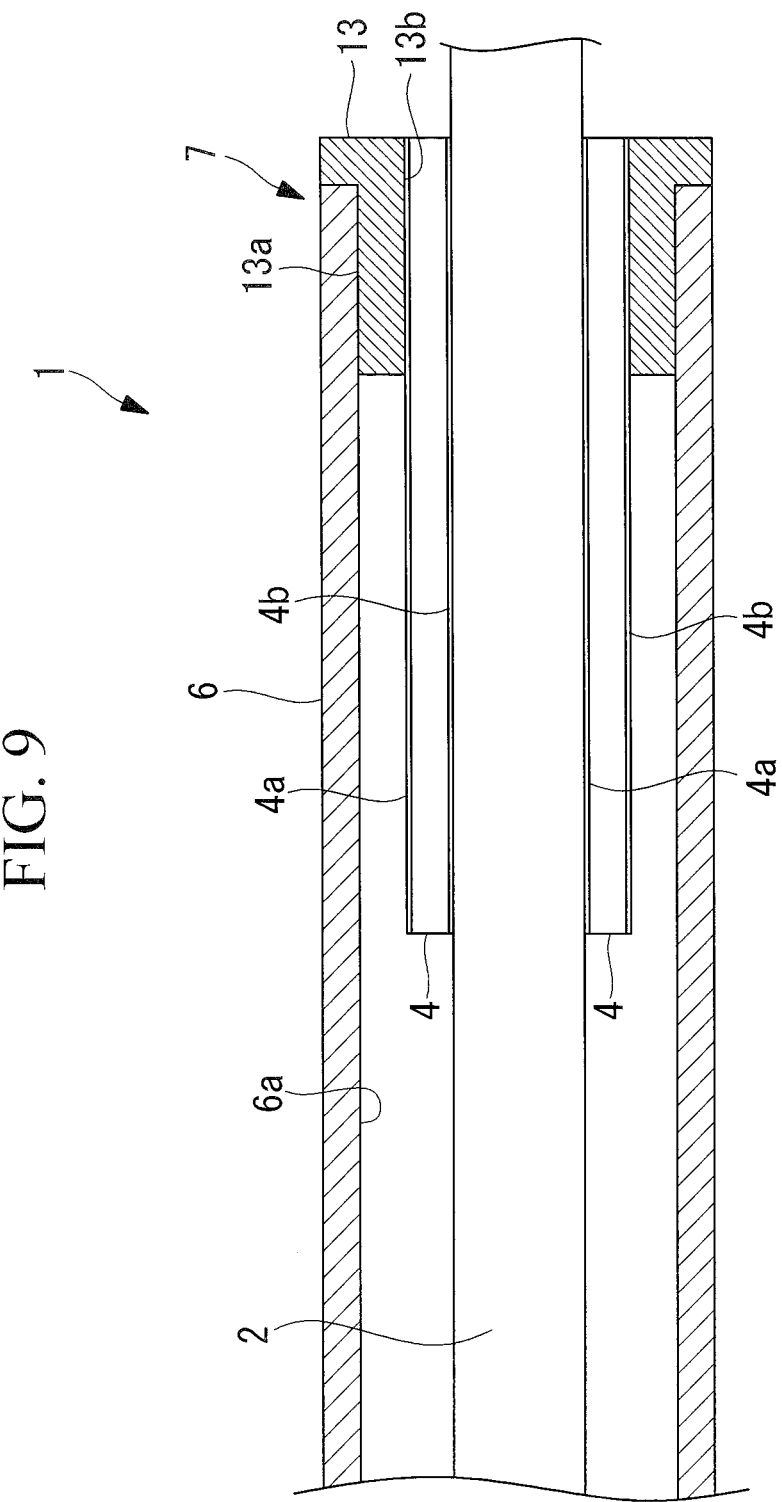
FIG. 9 is a longitudinal sectional view partially showing a fourth modification of the optical fiber scanner shown in FIG. 1.
Figure 10:
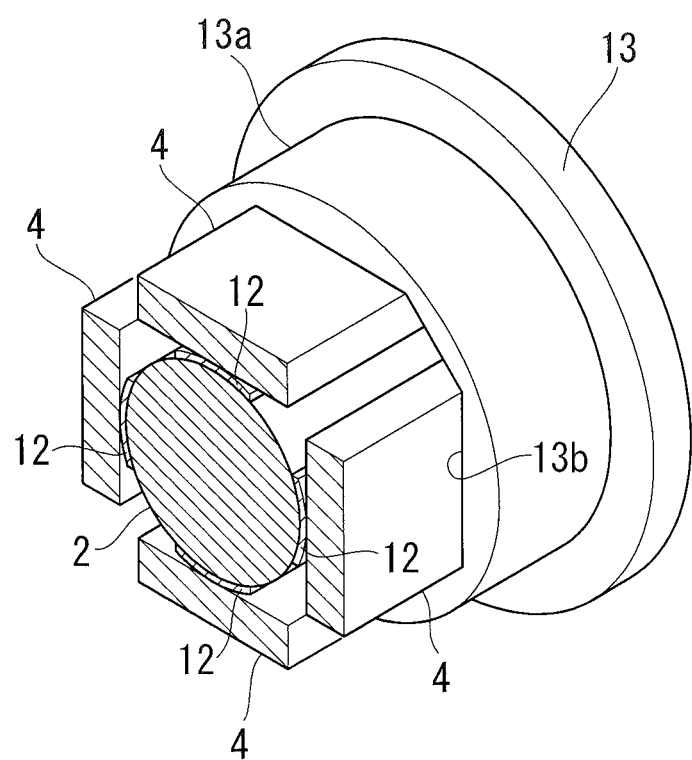
FIG. 10 is a perspective view showing a holding section used for an optical fiber scanner shown in FIG. 9.

Furthermore, as shown in FIGS. 9 and 10, it is possible to adopt, as a holding section, a holding section 13 having a fitting part 13a that is fitted into the inner surface of the inner hole 6a of the frame 6 and a through-hole 13b into which the assembly including the piezoelectric elements 4 and the optical fiber 2 is fitted. With this structure, it is possible to fix, to the frame 6, the piezoelectric elements 4 at an intermediate position in the longitudinal direction and to reduce the axial length of the optical fiber scanner 1.

Figure 11:
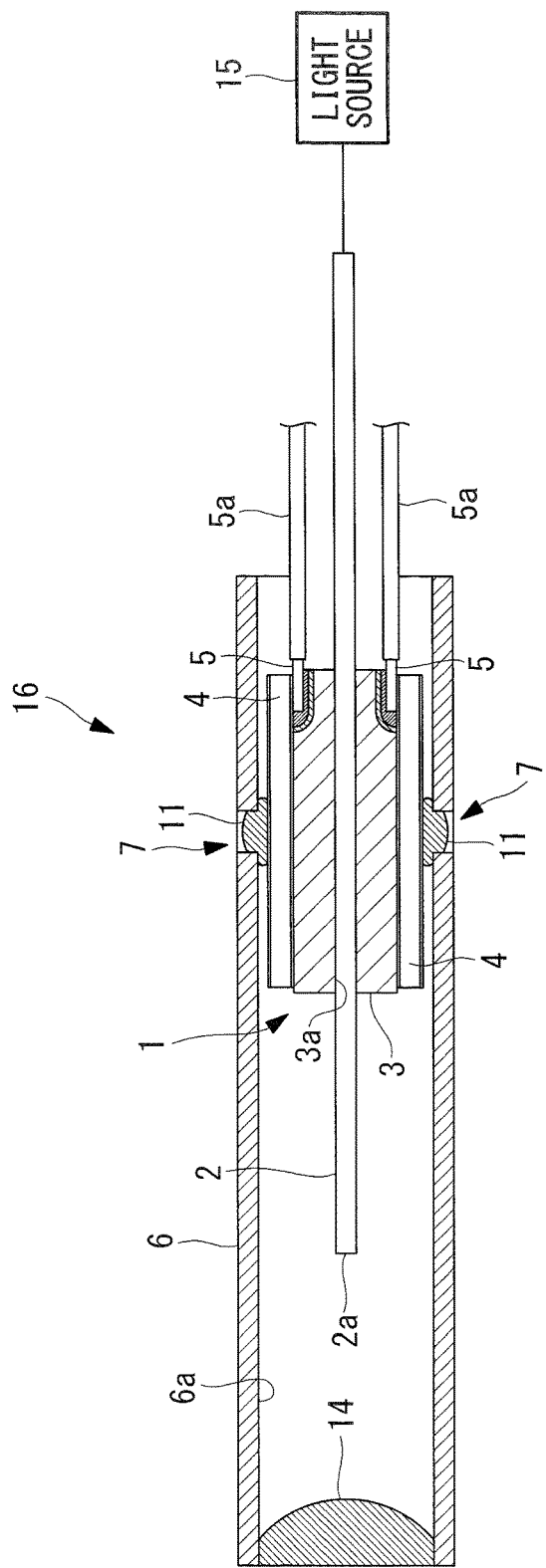
FIG. 11 is a longitudinal sectional view showing an illumination device according to one embodiment of the present invention.

Note that, as shown in FIG. 11, the optical fiber scanner 1 of this embodiment may be applied to an illumination device 16 that is provided with: a condenser lens 14 that condenses, at a position where a distal opening of the frame 6 is closed off, illumination light emitted from the emission end 2a of the optical fiber 2; and a light source 15 that provides illumination light to the optical fiber 2.

When the illumination light from the light source 15 is emitted from the emission end 2a of the optical fiber 2, the illumination light is condensed by the condenser lens 14, and a spot of light formed on an observation target can be scanned.

Figure 12:
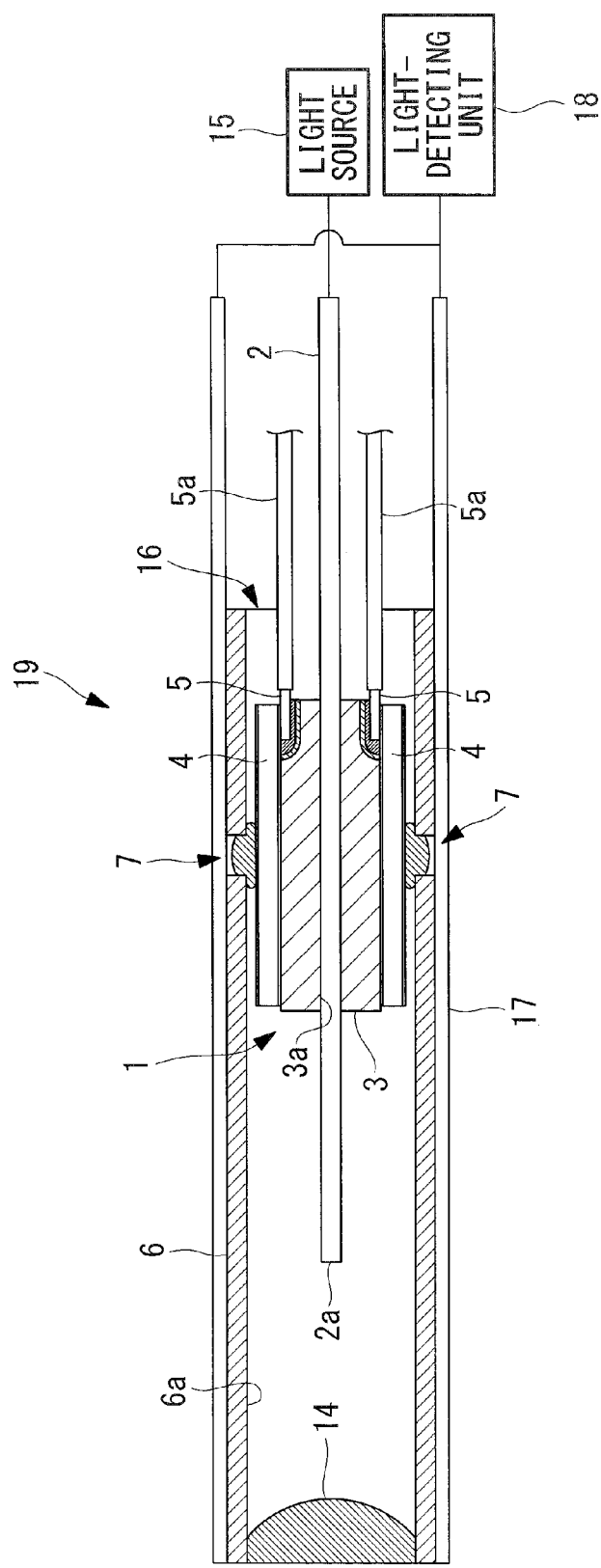
FIG. 12 is a longitudinal sectional view showing an observation apparatus according to one embodiment of the present invention.

Furthermore, as shown in FIG. 12, the optical fiber scanner 1 of this embodiment may be applied to an observation apparatus 19 that is provided with: a plurality of light-receiving fibers 17 arrayed on the outer periphery of the frame 6 in the circumferential direction; and a light-detecting unit 18 that detects return light received by the light-receiving fibers 17.

Return light (reflected light, fluorescence, or the like) returning from a scanning position of the spot of light scanned by the optical fiber scanner 1 is received by the light-receiving fibers 17, and the intensity thereof is detected by the light-detecting unit 18. Accordingly, the scanning position of the illumination light and the intensity of the return light are stored in association with each other, thereby making it possible to acquire an image of an observation target.

According to the illumination device 16 and the observation apparatus 19 of this embodiment, because the optical fiber scanner 1 is formed to have an extremely narrow diameter, the illumination device 16 and the observation apparatus 19 can also be formed to have an extremely narrow diameter and thus can be easily introduced into a narrow organ, such as a blood vessel, to perform illumination or observation.

The above-described embodiment leads to the following inventions.

According to one aspect, the present invention provides an optical fiber scanner including: an optical fiber that guides illumination light; a piezoelectric element that is disposed at an intermediate position on the optical fiber in the long-axis direction and that displaces, due to a bending vibration, an emission end of the optical fiber in a direction intersecting the long axis; a wiring part that is electrically bonded to the piezoelectric element at a location between the piezoelectric element and the optical fiber; a tube-shaped electrically conductive frame that has an inner hole for accommodating the piezoelectric element and the optical fiber; and a holding section that fixes the frame and the piezoelectric element and that conducts electricity between the frame and the piezoelectric element.

According to this aspect, an electrical current supplied from the wiring part flows from an optical-fiber side of the piezoelectric element to a frame-body side thereof in the thickness direction and flows into the frame via the holding section, which conducts electricity between the frame and the piezoelectric element. Accordingly, the piezoelectric element is made to produce a bending vibration in which the holding section serves as a node of the vibration, in a way according to the magnitude and the period of the electrical current, and thus the emission end of the optical fiber can be displaced in a direction intersecting the long axis. In this case, because the surface of the piezoelectric element closer to the frame and the inner surface of the frame have the same potential, even if they are brought into contact, a short circuit does not occur, and thus they can be brought sufficiently close to each other. Specifically, the inner surface of the inner hole of the frame can be brought close to the piezoelectric element so as to have a gap allowing a vibration of the piezoelectric element that is required to cause the emission end of the optical fiber to produce a desired amplitude displacement, thus making it possible to achieve a sufficient reduction in diameter.

In the above-described aspect, it is also possible to further include a tube-shaped vibration transmission member that has a through-hole through which the optical fiber passes and that is formed of an electrically insulating material, in which the piezoelectric element may be bonded to an outer face of the vibration transmission member, through which the optical fiber passes.

By doing so, the bending vibration of the piezoelectric element is transferred to the optical fiber via the vibration transmission member, thus making it possible to more reliably displace the emission end of the optical fiber. With a vibration transmission member that is formed of an electrically insulating material, wiring parts connected to piezoelectric elements can be isolated from each other.

Furthermore, in the above-described aspect, a concave section for accommodating a joint part for joining the wiring part and the piezoelectric element may be provided in a bonding face of the vibration transmission member, to which the piezoelectric element is bonded.

By doing so, because the joint part for joining the wiring part to the piezoelectric element is accommodated in the concave section provided on the vibration transmission member, it is possible to prevent the diameter of the inner hole of the frame from being limited by bulging of the joint part and to achieve a reduction in diameter.

Furthermore, in the above-described aspect, the wiring part may be formed into a thin film on a surface of the optical fiber; and the piezoelectric element may be bonded to the optical fiber, with the wiring part being sandwiched therebetween.

By doing so, because the vibration transmission member is not interposed between the surface of the optical fiber and the piezoelectric element, and the wiring part is formed into the thin film, the outer size can be minimized to achieve a reduction in diameter.

Furthermore, in the above-described aspect, the holding section may be a caulking section that is formed by pressing the frame from a radially outer side to a radially inner side.

By doing so, with the assembly including the optical fiber and the piezoelectric element being accommodated in the frame, the frame is pressed from outside and is deformed to form the caulking section, thereby making it possible to facilitate manufacturing.

Furthermore, in the above-described aspect, the holding section may be an electrically conductive adhesive filled in a gap between the frame and the piezoelectric element.

By doing so, with the assembly including the optical fiber and the piezoelectric element being accommodated in the frame, an electrically conductive adhesive is merely filled in a gap between the frame and the piezoelectric element, thereby making it possible to form the holding section and to facilitate manufacturing.

Furthermore, in the above-described aspect, the holding section may be provided with: a through-hole into which an assembly of the piezoelectric element and the optical fiber is fitted; and a fitting part that is fitted into the inner hole of the frame.

By doing so, the assembly including the piezoelectric element and the optical fiber is made to pass through the through-hole of the holding section, and the fitting part is fitted into the inner hole of the frame, thereby making it possible to facilitate manufacturing.

Furthermore, according to another aspect, the present invention provides an illumination device including: a light source that produces illumination light; and one of the above-described optical fiber scanners for scanning the illumination light from the light source.

Furthermore, according to still another aspect, the present invention provides an observation apparatus including: the above-described illumination device; and a light-detecting unit that detects return light returning from a subject irradiated with illumination light from the illumination device.

REFERENCE SIGNS LIST 1 optical fiber scanner
2 optical fiber
2a emission end
3 ferrule (vibration transmission member)
3a through-hole
4 piezoelectric element
5 lead wire (wiring part)
6 frame
6a inner hole
6c caulking section
7 holding section
8 joint part
9 concave section
11 electrically conductive adhesive (adhesive)
12 thin film (wiring part)
13a fitting part
13b through-hole
15 light source
16 illumination device
18 light-detecting unit
19 observation apparatus

The invention claimed is:

1. An optical fiber scanner comprising:
an optical fiber that guides illumination light;
a piezoelectric element that is disposed at an intermediate position on the optical fiber in the long-axis direction and that displaces, due to a bending vibration, an emission end of the optical fiber in a direction intersecting the long axis;
a wiring part that is electrically bonded to the piezoelectric element at a location between the piezoelectric element and the optical fiber;
a tube-shaped electrically conductive frame that has an inner hole for accommodating the piezoelectric element and the optical fiber; and
a holding section that fixes the frame and the piezoelectric element and that conducts electricity between the frame and the piezoelectric element.

2. An optical fiber scanner according to claim 1, further comprising a tube-shaped vibration transmission member that has a through-hole through which the optical fiber passes and that is formed of an electrically insulating material,
wherein the piezoelectric element is bonded to an outer face of the vibration transmission member, through which the optical fiber passes.

3. An optical fiber scanner according to claim 2, wherein a concave section for accommodating a joint part for joining the wiring part and the piezoelectric element is provided in a bonding face of the vibration transmission member, to which the piezoelectric element is bonded.

4. An optical fiber scanner according to claim 1,
wherein the wiring part is formed into a thin film on a surface of the optical fiber; and
the piezoelectric element is bonded to the optical fiber, with the wiring part being sandwiched therebetween.

5. An optical fiber scanner according to claim 1, wherein the holding section is a caulking section that is formed by pressing the frame from a radially outer side to a radially inner side.

6. An optical fiber scanner according to claim 1, wherein the holding section is an electrically conductive adhesive filled in a gap between the frame and the piezoelectric element.

7. An optical fiber scanner according to claim 1, wherein the holding section is provided with: a through-hole into which an assembly of the piezoelectric element and the optical fiber is fitted; and a fitting part that is fitted into the inner hole of the frame.

8. An illumination device comprising:
a light source that produces illumination light; and
an optical fiber scanner according to claim 1, for scanning the illumination light from the light source.

9. An observation apparatus comprising:
an illumination device according to claim 8; and
a light-detecting unit that detects return light returning from a subject irradiated with illumination light from the illumination device.

* * * * *